(12) United States Patent
Azuma

(10) Patent No.: US 8,071,914 B2
(45) Date of Patent: Dec. 6, 2011

(54) HEATING APPARATUS

(75) Inventor: Hidetaka Azuma, Toyonaka (JP)

(73) Assignees: Noboru Oshima, Nara, Nara Prefecture (JP); J. C. Jordan, El Dorado Hills, CA (US)

( * ) Notice: Subject to any disclaimer, the term of this patent is extended or adjusted under 35 U.S.C. 154(b) by 878 days.

(21) Appl. No.: 11/964,362

(22) Filed: Dec. 26, 2007

(65) Prior Publication Data

US 2009/0166352 A1 Jul. 2, 2009

(51) Int. Cl.
*H05B 11/00* (2006.01)
*H01J 1/02* (2006.01)

(52) U.S. Cl. .......................... 219/220; 313/15

(58) Field of Classification Search .................. 219/220, 219/219, 201, 230; 313/15; 362/92; 977/904, 977/905–931; 424/464–483
See application file for complete search history.

(56) References Cited

U.S. PATENT DOCUMENTS

| | | |
|---|---|---|
| 4,002,881 A | 1/1977 | West |
| 4,791,262 A | 12/1988 | Masao et al. |
| 4,855,552 A | 8/1989 | Marceau |
| 5,142,115 A | 8/1992 | Weidman et al. |
| 5,216,215 A | 6/1993 | Walker |
| 6,118,111 A | 9/2000 | Price et al. |
| 6,512,212 B1 | 1/2003 | Harris |
| 7,868,134 B2 * | 1/2011 | Winkler et al. ................ 530/300 |
| 2001/0047074 A1 * | 11/2001 | Kissel et al. ................... 528/272 |
| 2004/0149742 A1 | 8/2004 | Lescano |
| 2006/0228414 A1 * | 10/2006 | Cook ............................. 424/469 |
| 2007/0102421 A1 | 5/2007 | Tonomura |
| 2009/0209453 A1 * | 8/2009 | Moyle ................................. 514/8 |
| 2010/0290982 A1 * | 11/2010 | Ranjan et al. ................. 424/1.11 |
| 2011/0008304 A1 * | 1/2011 | Troyer et al. ................ 424/93.71 |

FOREIGN PATENT DOCUMENTS

| | | |
|---|---|---|
| EP | 0193843 A1 | 9/1986 |
| WO | PCT/US99/17900 | 8/1999 |

* cited by examiner

*Primary Examiner* — Daniel L Robinson
(74) *Attorney, Agent, or Firm* — Law Offices of David M. Lang; David M. Lang

(57) ABSTRACT

An apparatus for efficient heating liquids or gases comprising of a transformer having a primary and secondary winding wherein the secondary winding forms a shorted heating element having a resistance in the range of 1.6730 $\mu\Omega$·cm to 185 $\mu\Omega$·cm, permitting liquid or gas to pass therethrough, whereby the liquid or gas is heated and heat transfer may be optionally facilitated through use of disc filters disposed within said heating element promoting turbulent flow which aids in mixing and more efficient thermal transfer. In an alternative embodiment, the heating element is not the secondary winding but another portion of the circuit on the alienation side of the transformer. The heating element may be comprised of a variety of sizes, shapes, and materials. In an alternative embodiment, the alienation side of the transformer may have a reverse winding which cancels reactive currents generated in the secondary winding.

16 Claims, 22 Drawing Sheets

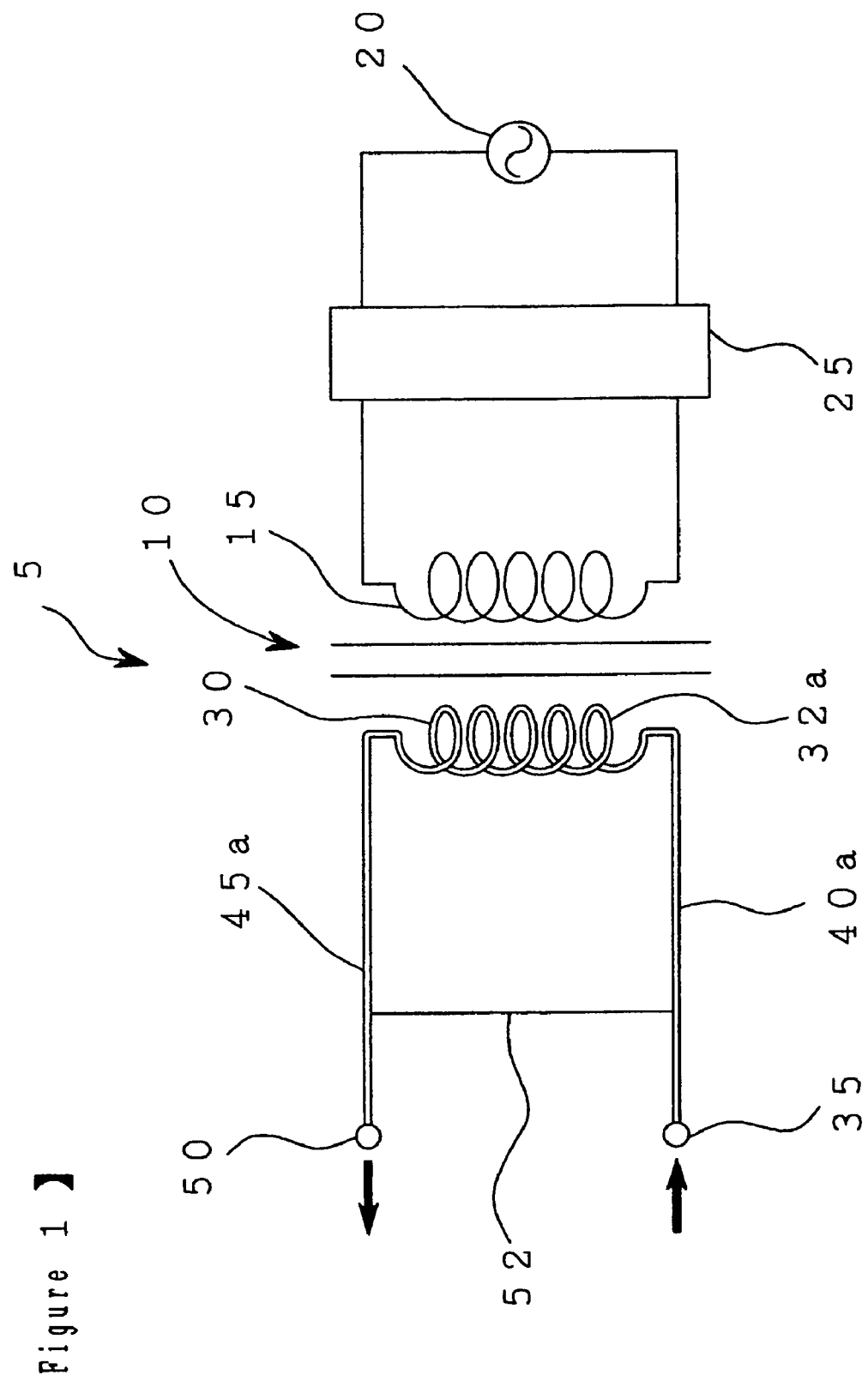
[ Figure 1 ]

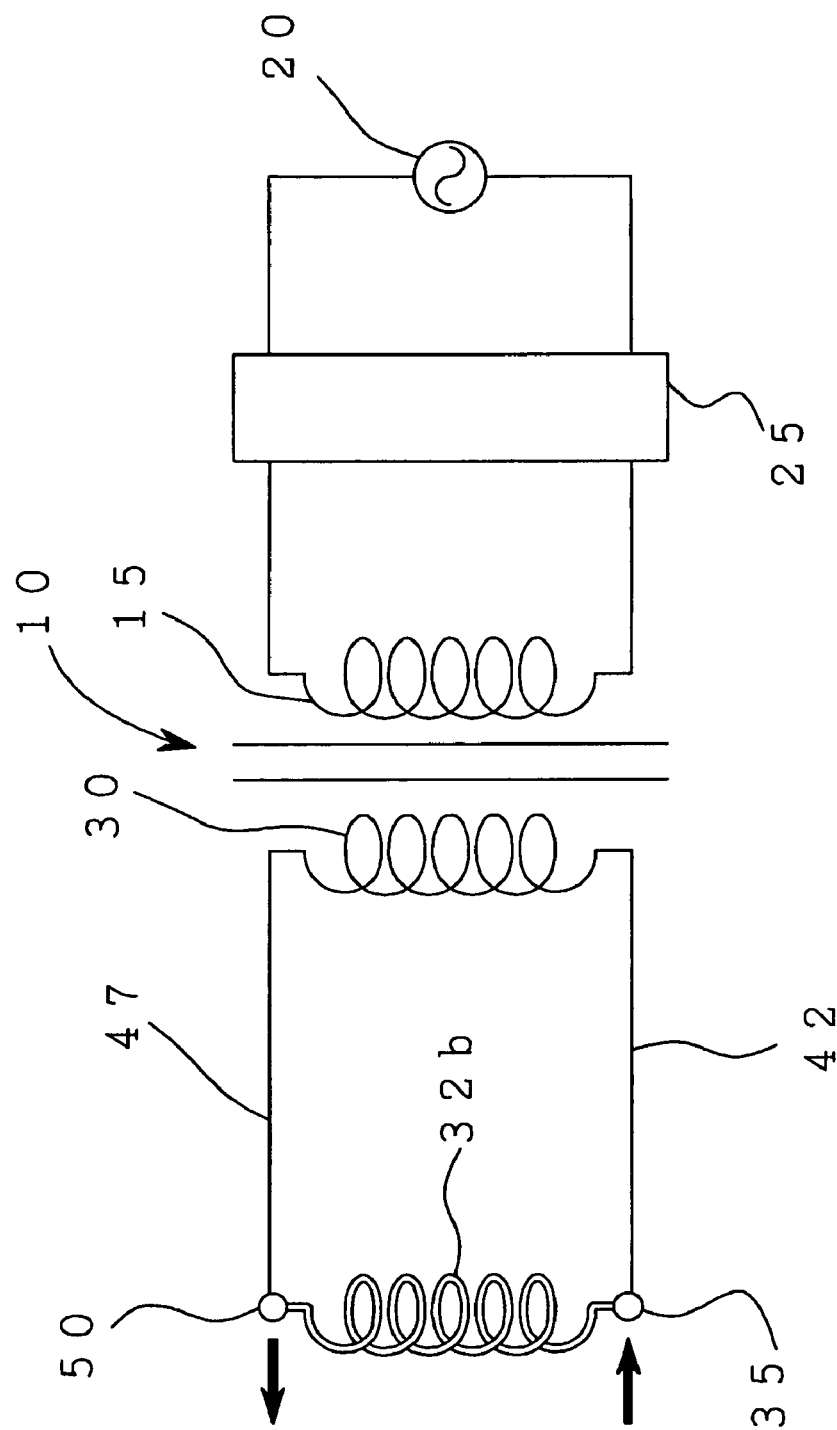
[Figure 2]

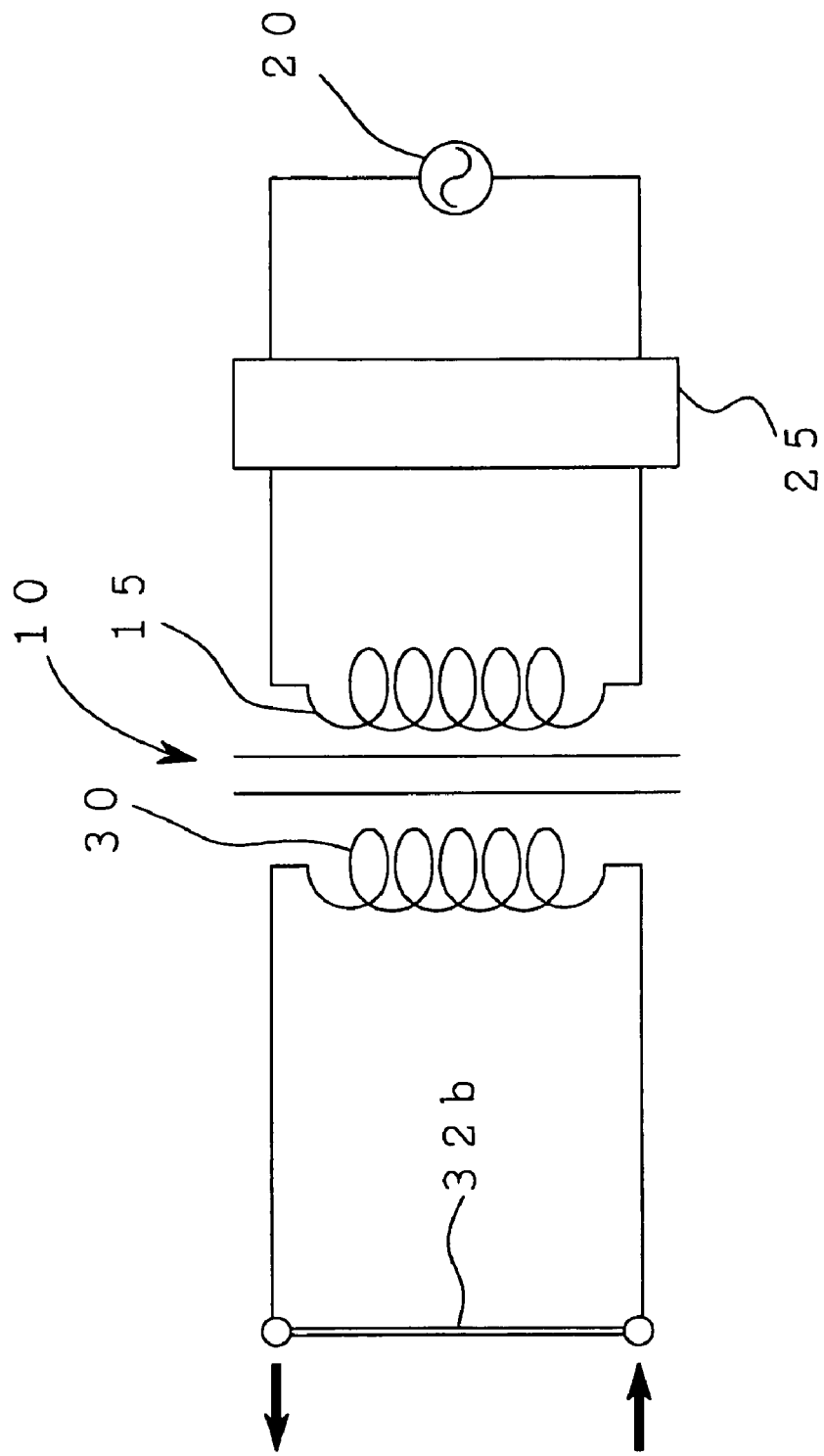
[Figure 3]

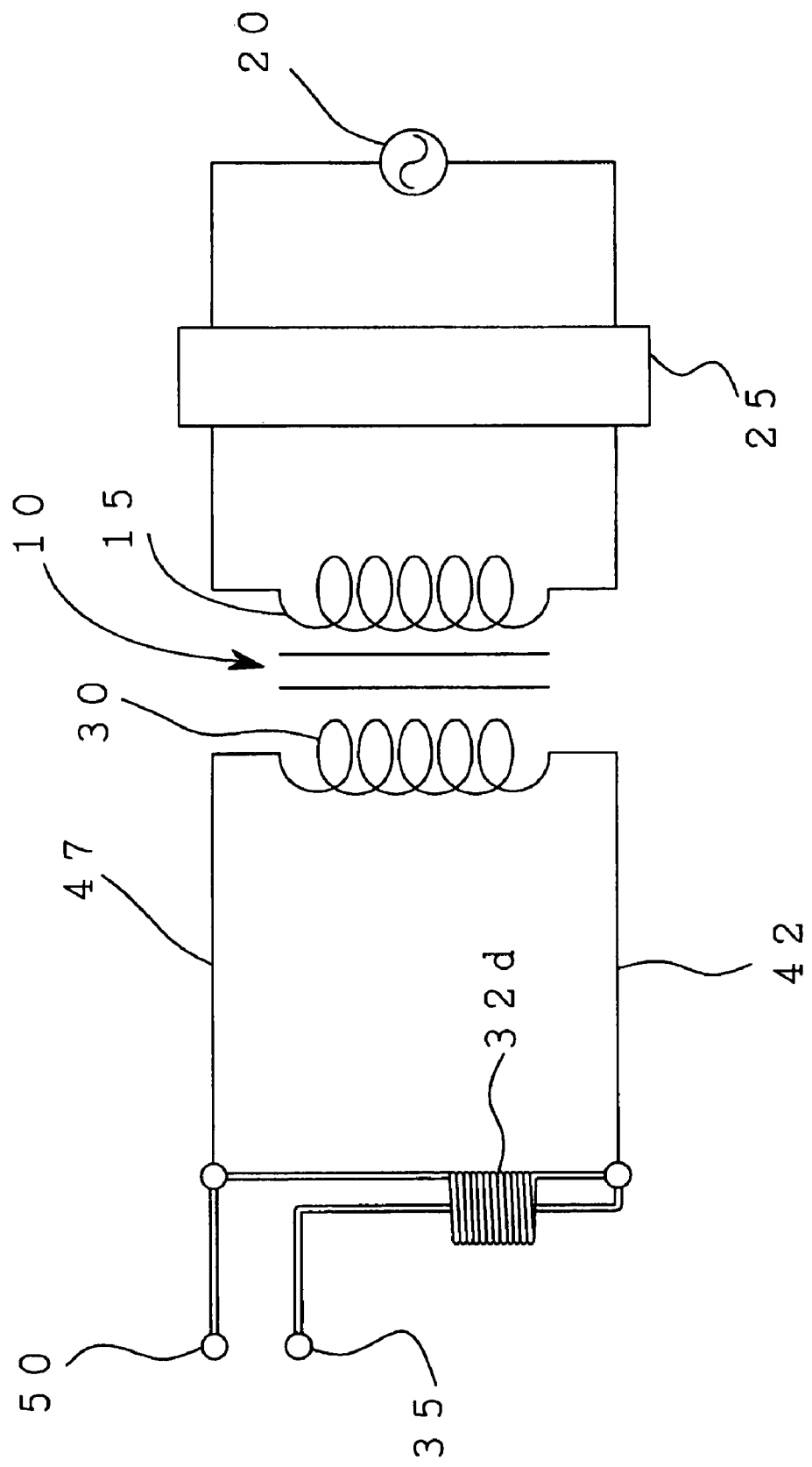
[Figure 4]

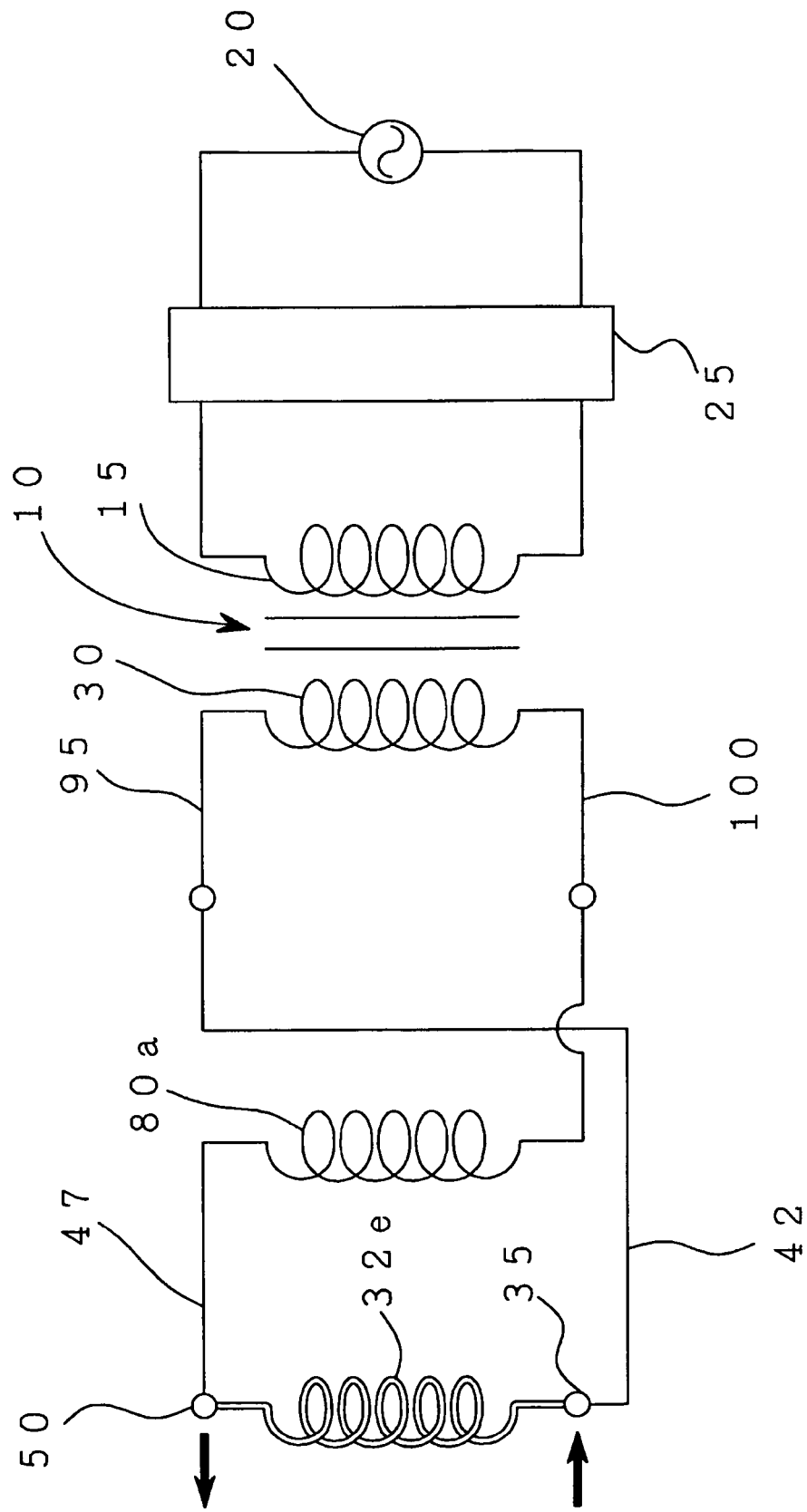
[Figure 5]

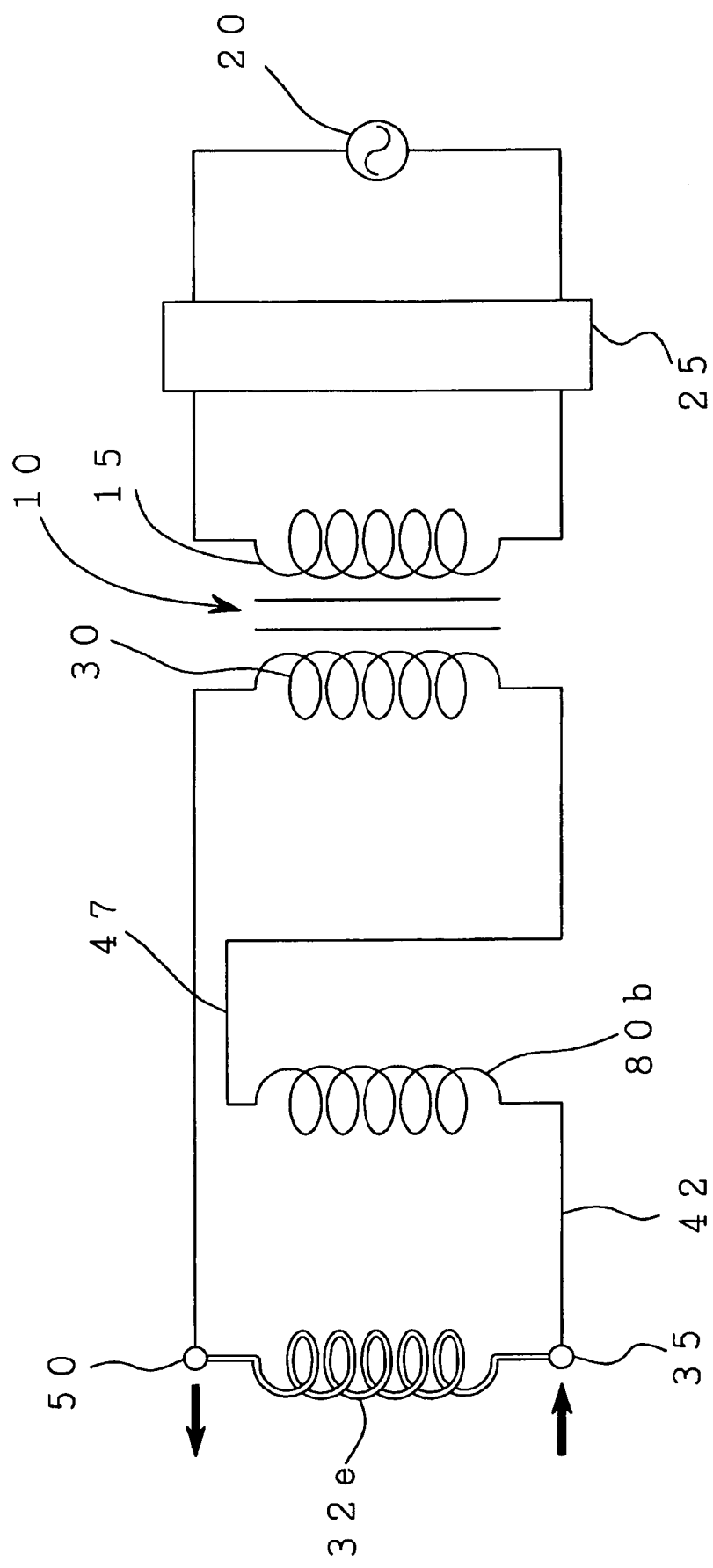
[Figure 6]

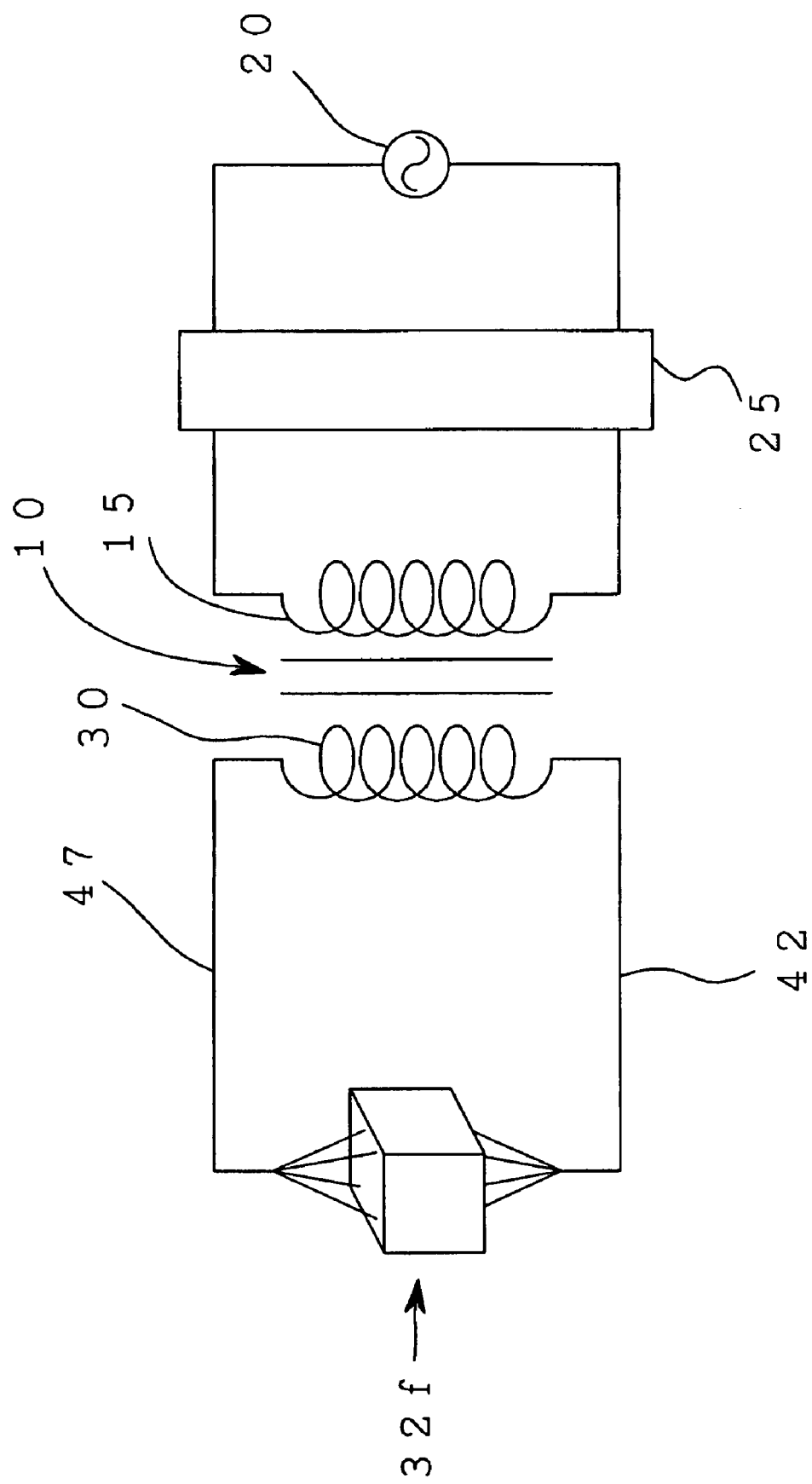
[Figure 7]

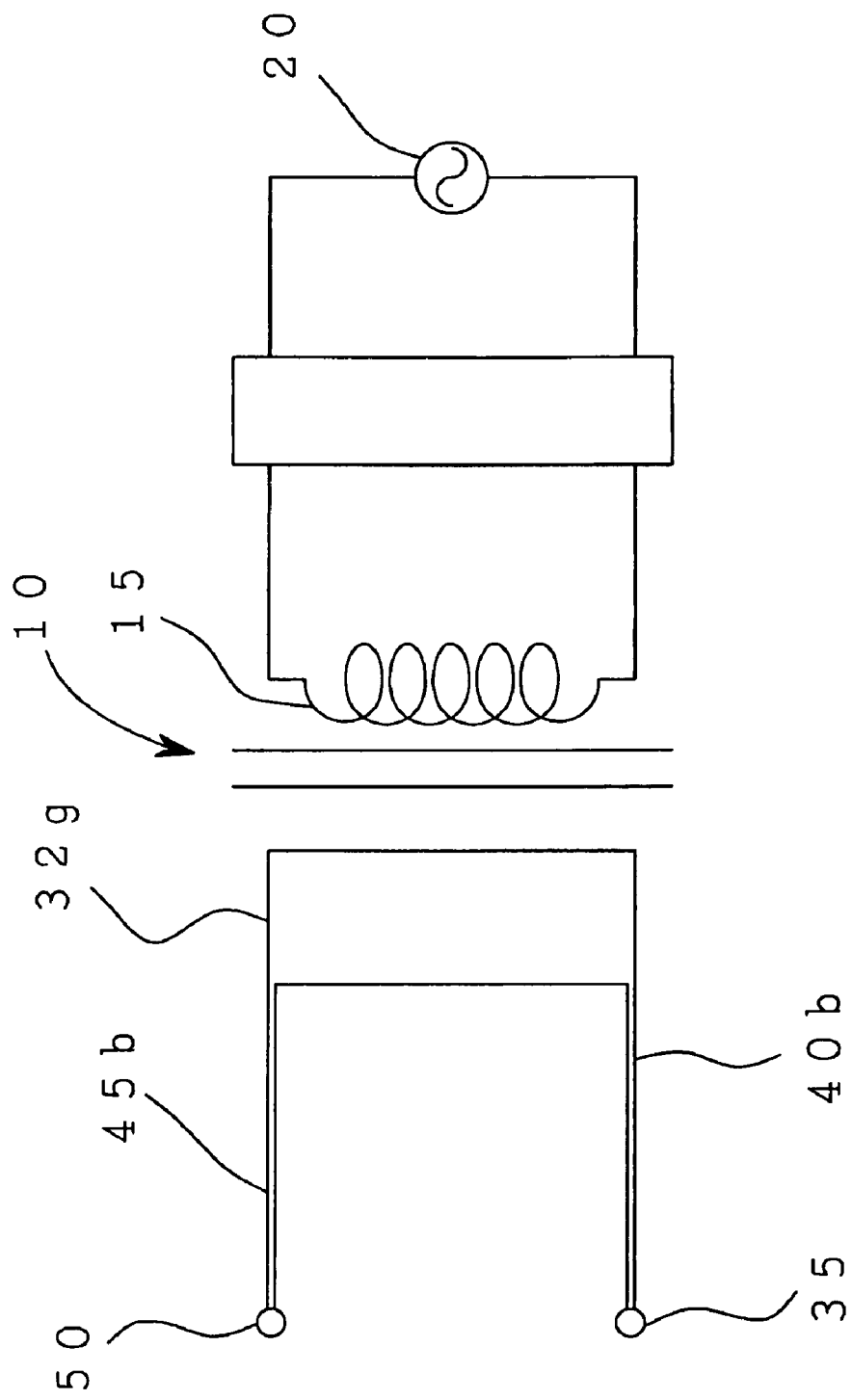
[Figure 8]

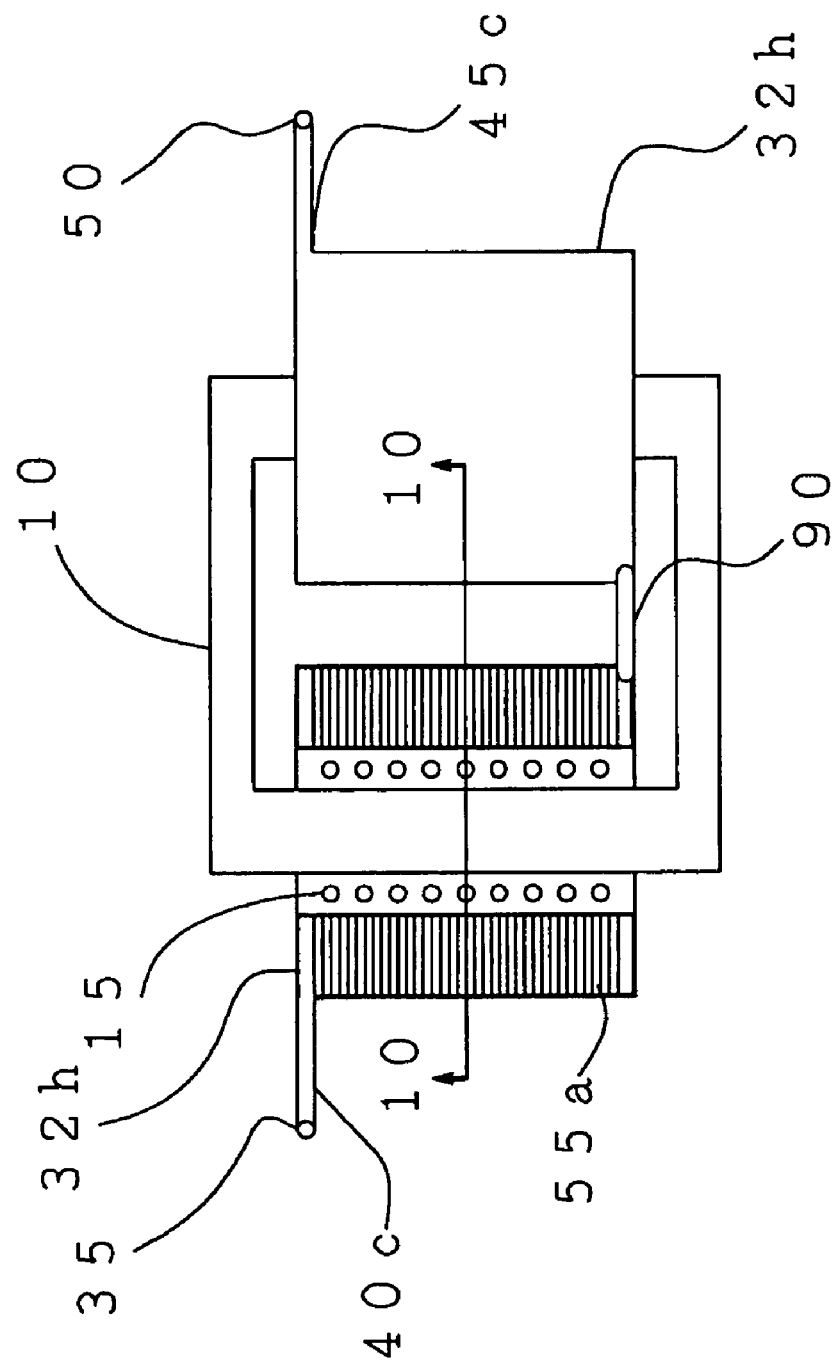
[Figure 9]

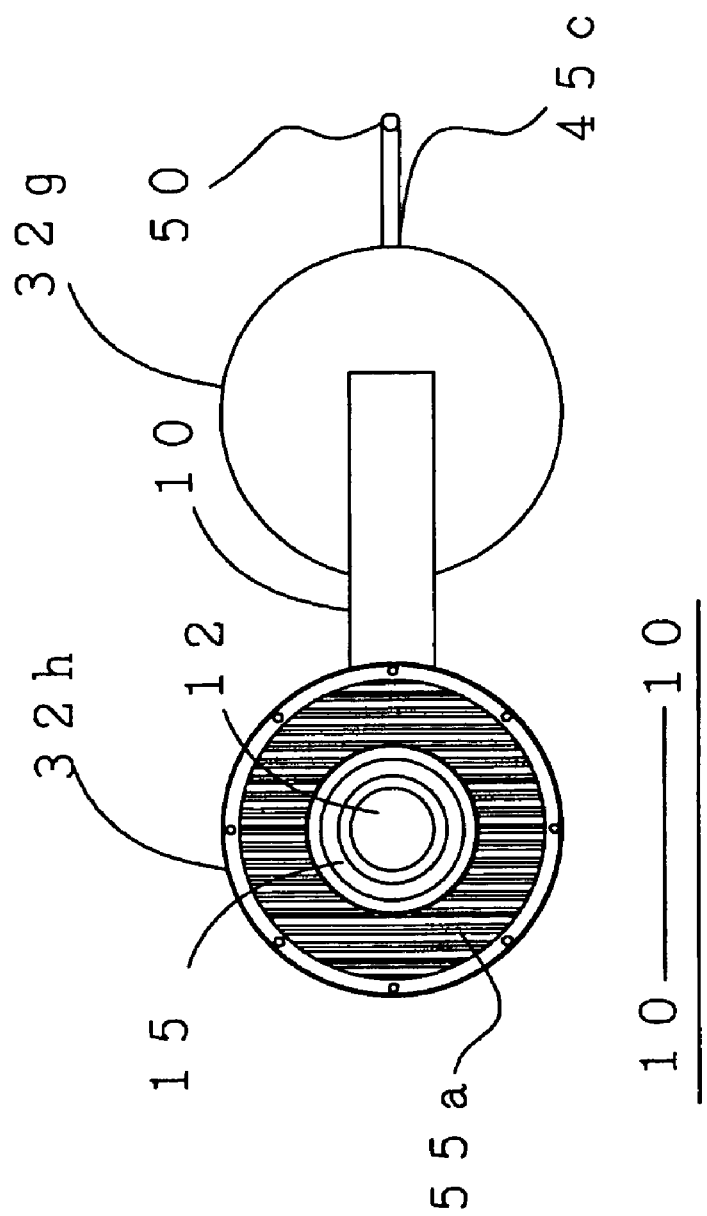
[Figure 10]

[Figure 11]
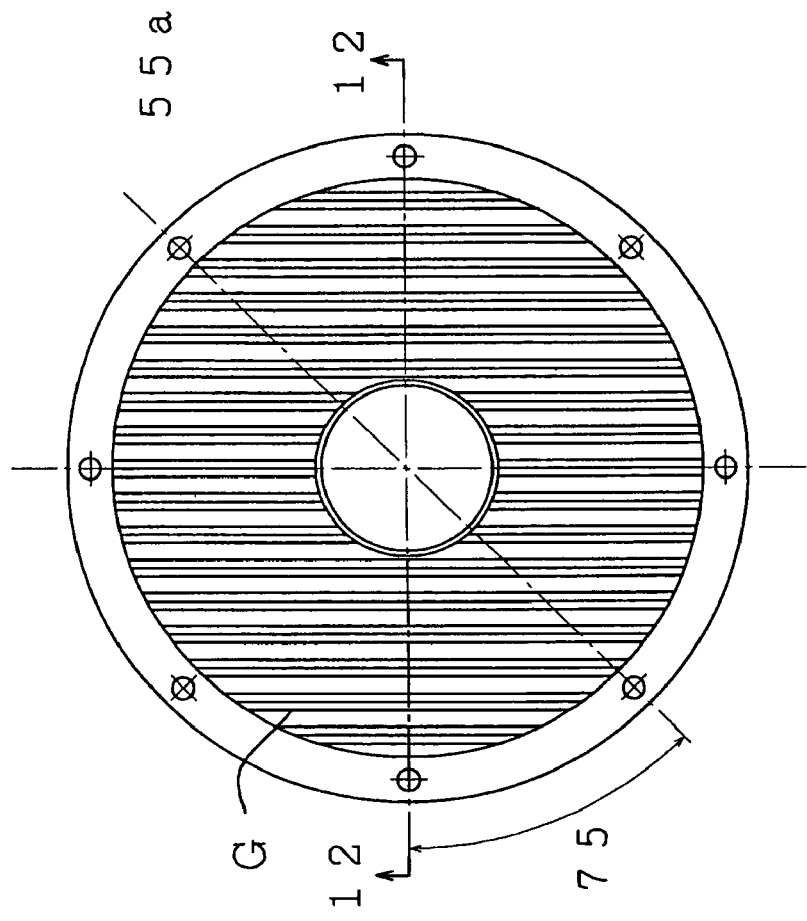
[Figure 12]
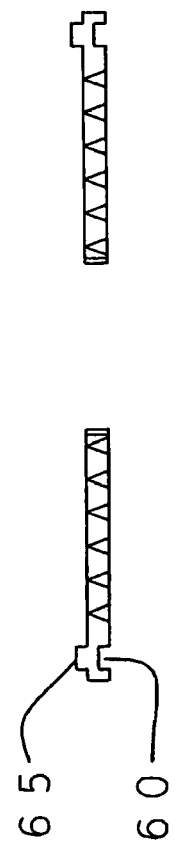

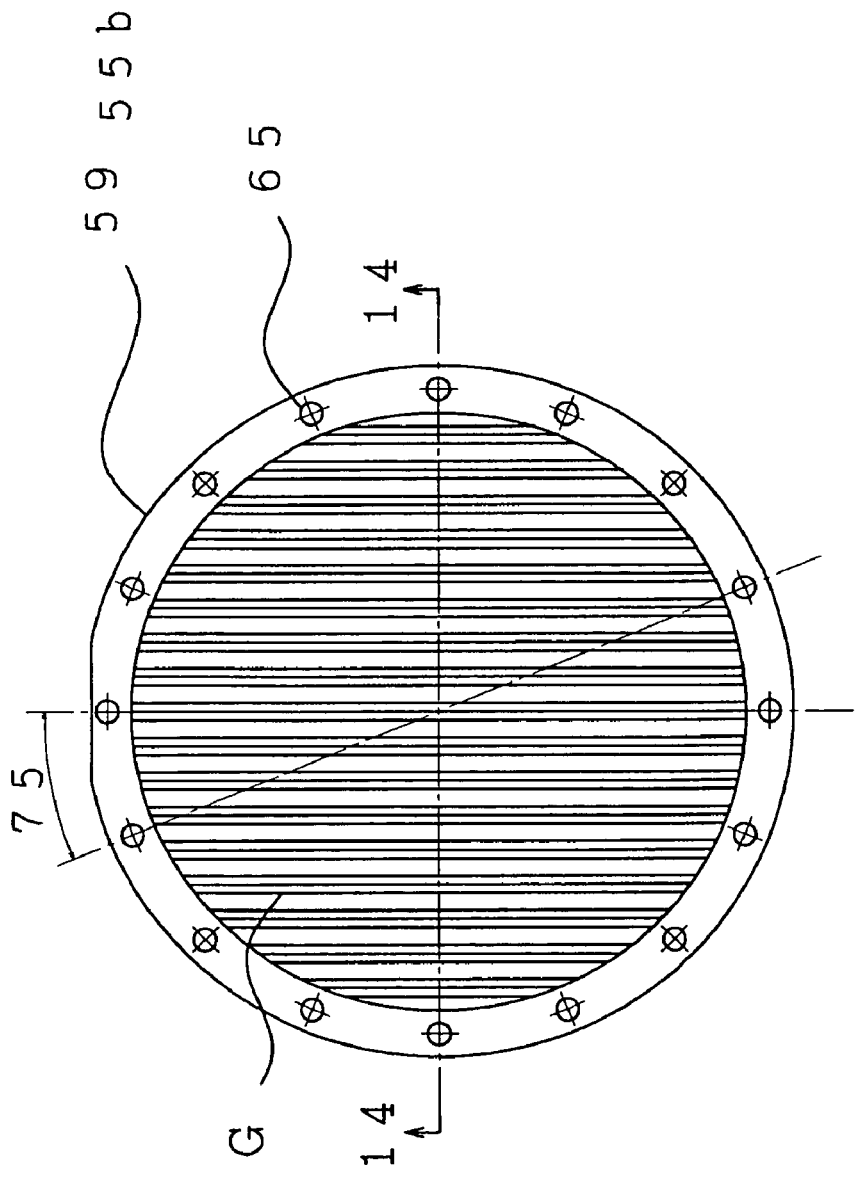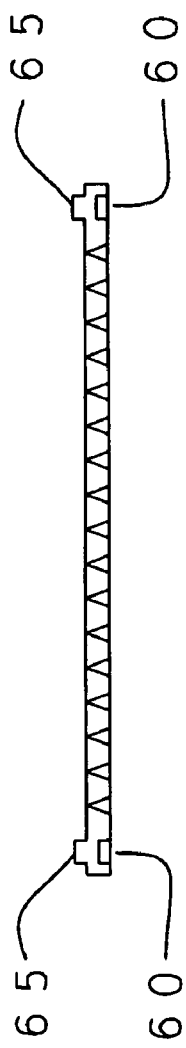

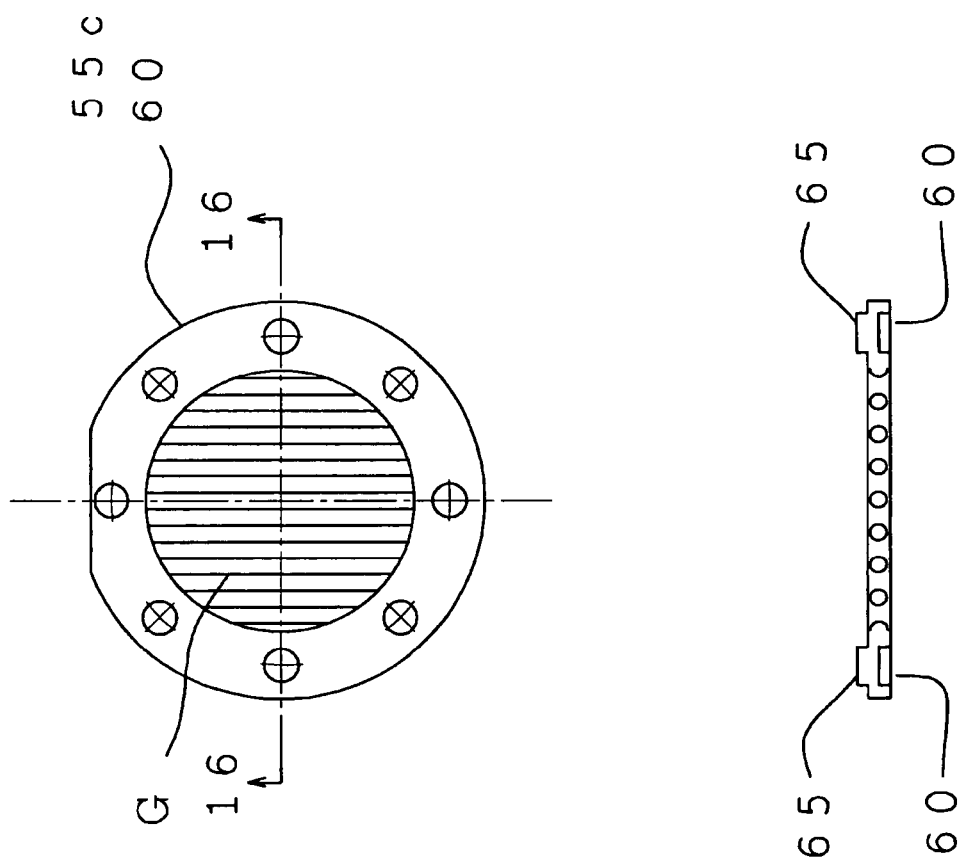

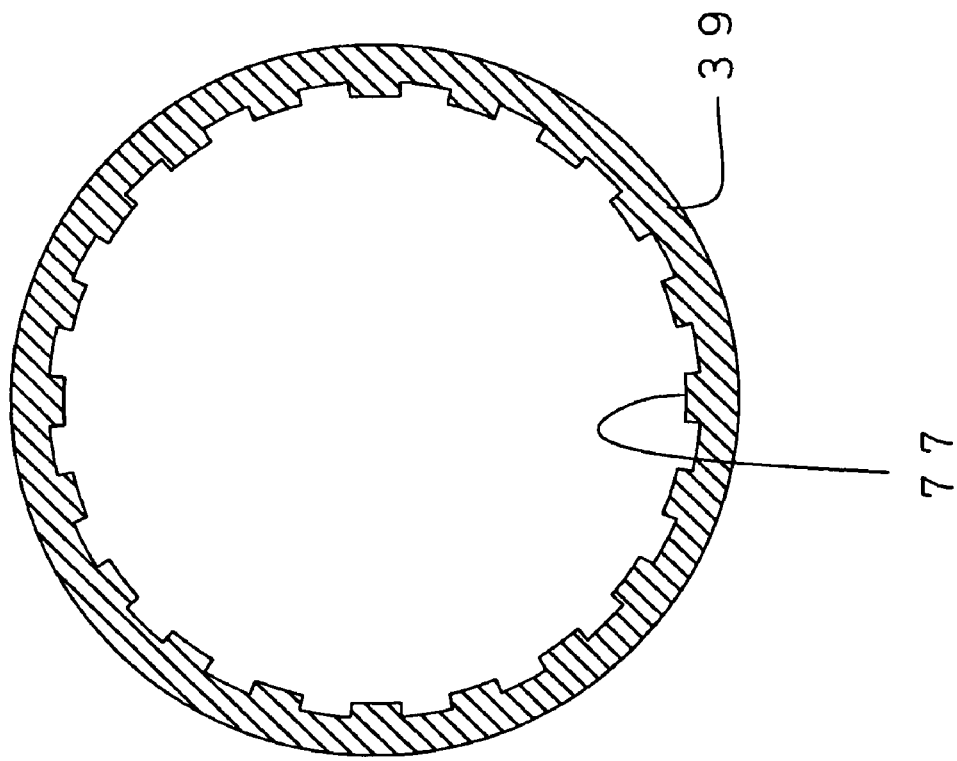
[Figure 17]

FIG. 18 Estimated Supply Capacity (Table of Capacity)

| power KW | supply temperature | quantity of water/min output volume/mm or temperature of output water | | | | | | |
|---|---|---|---|---|---|---|---|---|
| | | 3 liter | 4 liter | 5 liter | 6 liter | 7 liter | 8 liter |
| 10 KW | 5°C | 50~53°C | 38~41°C | 31~33°C | 27~29°C | 23~25°C | 21~23°C |
| | 10 | 55~58 | 42~46 | 36~38 | 32~34 | 28~30 | 26~28 |
| | 15 | 60~63 | 49~52 | 41~43 | 37~39 | 33~35 | 31~33 |
| | 20 | 65~68 | 53~56 | 46~48 | 42~44 | 38~40 | 36~38 |
| 12 KW | 5°C | 59~62°C | 45~48°C | 37~39°C | 32~34°C | 28~30°C | 25~27°C |
| | 10 | 64~67 | 50~53 | 42~44 | 37~39 | 33~35 | 30~32 |
| | 15 | 70~73 | 55~58 | 47~49 | 42~44 | 38~40 | 35~37 |
| | 20 | 75~78 | 60~63 | 52~54 | 47~49 | 43~45 | 40~42 |
| 15 KW | 5°C | 74~77°C | 56~59°C | 46~48°C | 39~41°C | 34~36°C | 30~32°C |
| | 10 | 79~82 | 61~64 | 50~53 | 43~46 | 39~41 | 35~37 |
| | 15 | 84~87 | 65~69 | 55~58 | 48~51 | 44~46 | 40~42 |
| | 20 | 89~92 | 71~74 | 60~63 | 53~55 | 49~51 | 45~47 |
| 20 KW | 5°C | 96~boiling | 74~77°C | 59~62°C | 50~53°C | 43~46°C | 38~41°C |
| | 10 | 99~boiling | 78~82 | 64~67 | 55~58 | 48~51 | 44~47 |
| | 15 | boiling | 84~87 | 68~72 | 60~63 | 53~56 | 49~52 |
| | 20 | " | 88~92 | 74~77 | 65~68 | 58~61 | 54~57 |

Thermal Efficiency = 95%~99%

[Figure 19]

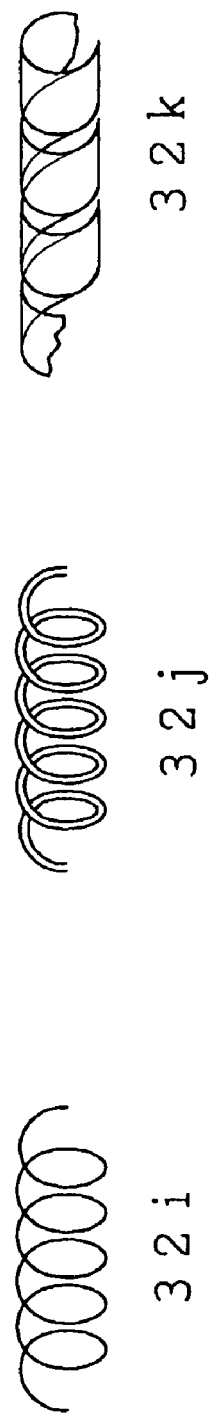
[Figure 20]

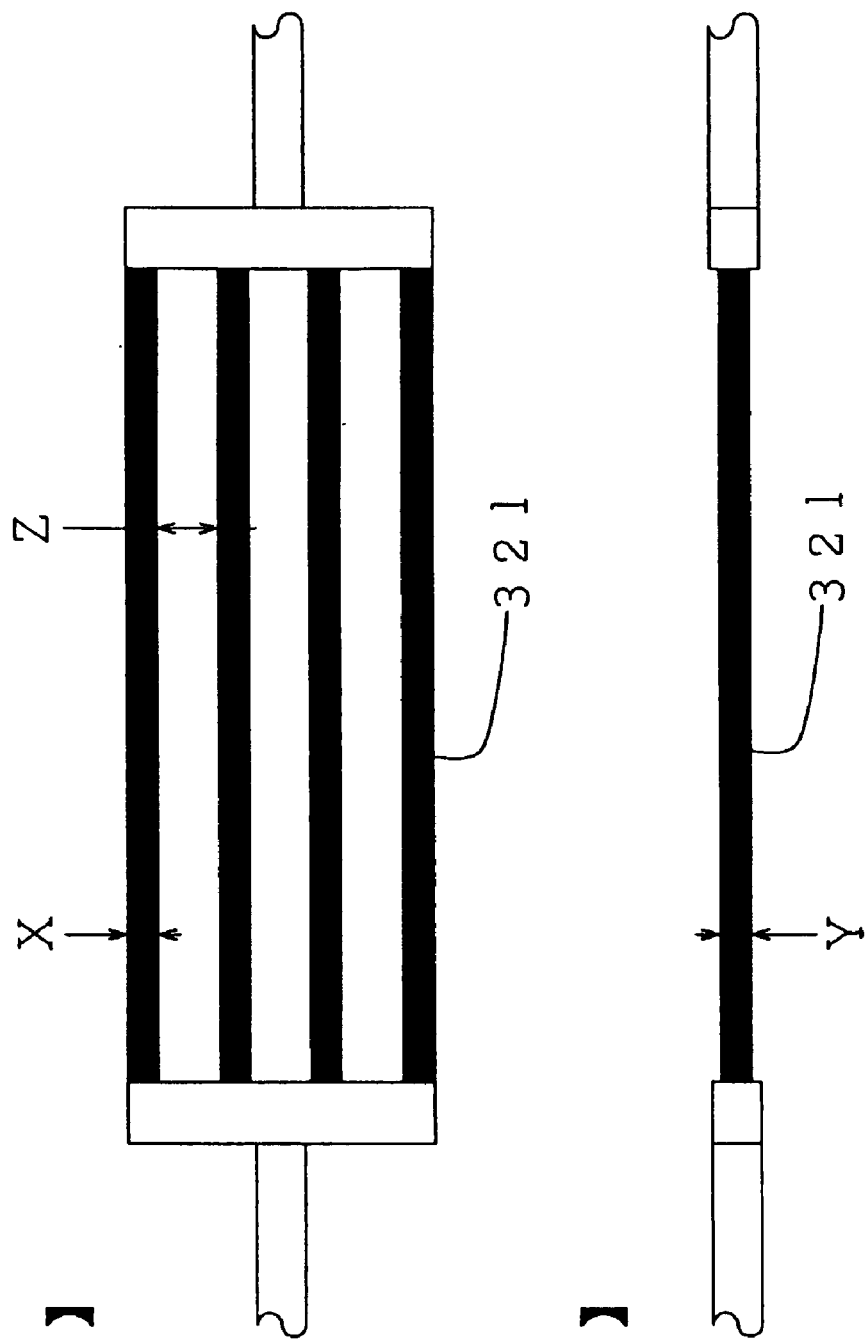
[Figure 21]
[Figure 22]

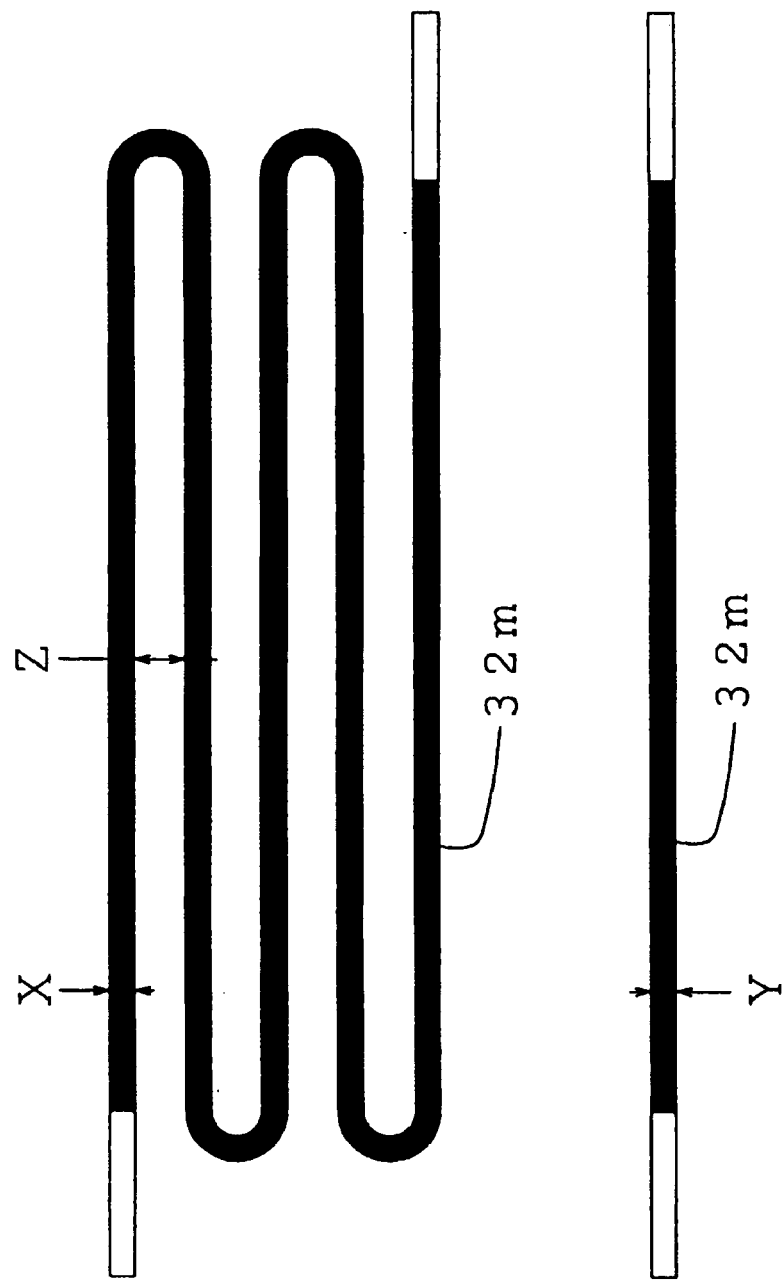
[Figure 23]
[Figure 24]

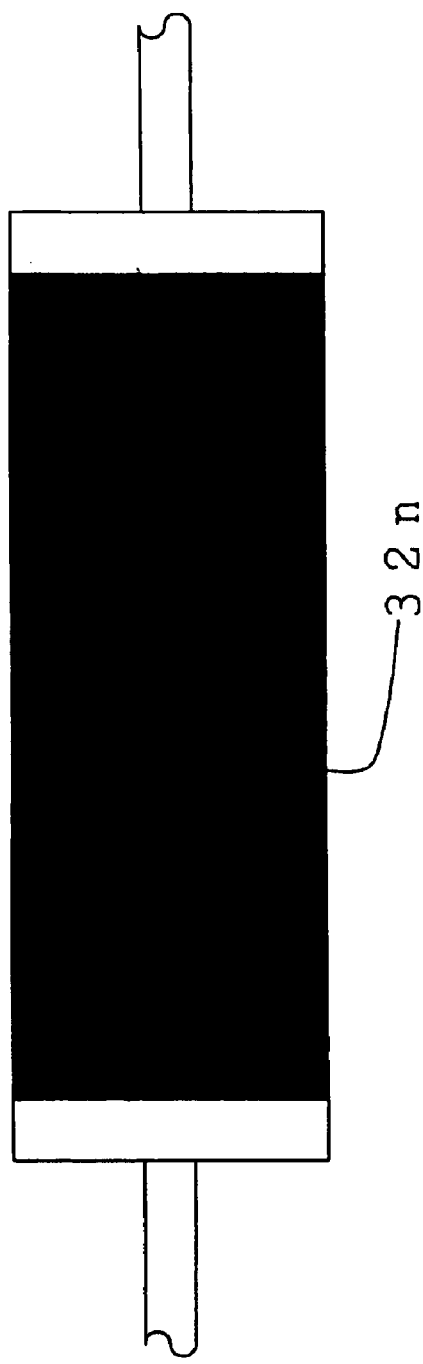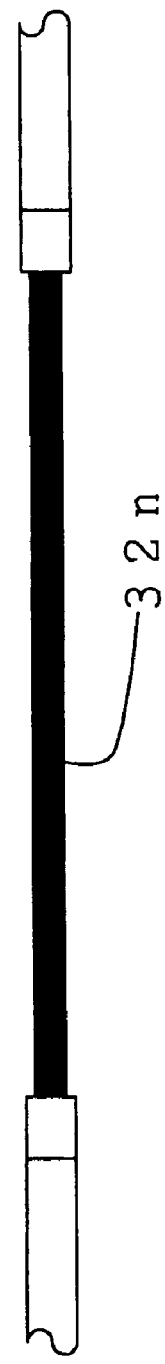
[Figure 25]
[Figure 26]

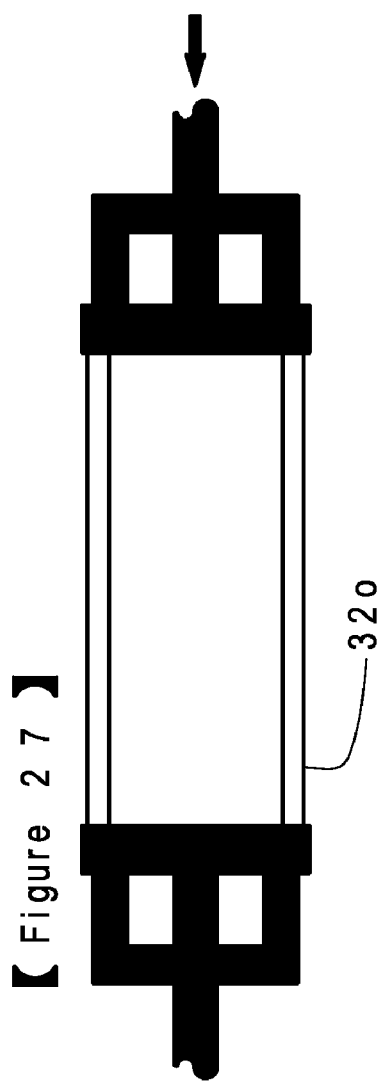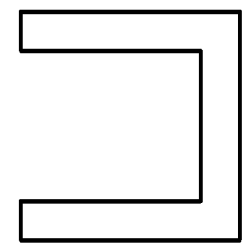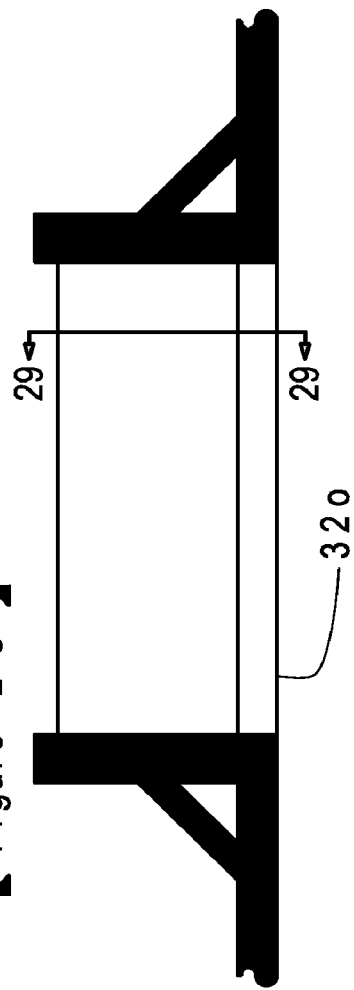

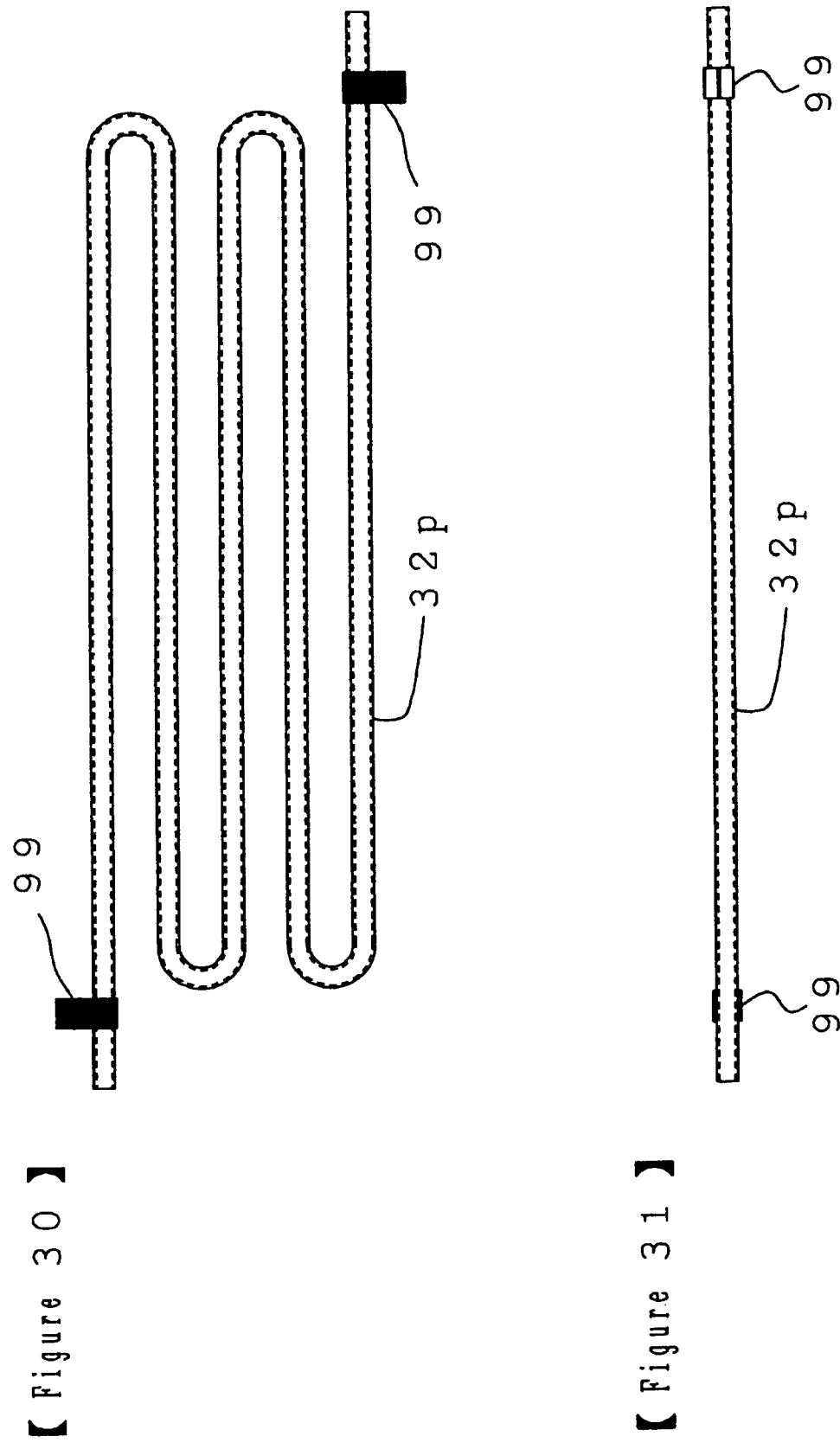

HEATING APPARATUS

FIELD OF THE INVENTION

The present invention relates to an apparatus for heating liquids and gases generally, and more specifically to an apparatus utilizing one or more strategies to improve heating efficiency through a preferred heating element, one or more means to promote fluid mixing and stirring, and cancellation or utilization of reactive currents where appropriate.

BACKGROUND

There is always a need for heated liquids and gases. Lack of efficiency in converting electric energy into usable thermal energy has been problematic. Electric heaters ultimately rely on fossil fuels to produce electricity, thus consumption of fossil fuels produces $CO^2$ that contributes to global warming. Therefore, when using electricity to produce heat, it is important to use that electricity sparingly and efficiently to minimize damage to the global environment.

The heating efficiency of many prior art devices varies considerably: between 40%-60% for nichrome wire heaters, and 60%-80% for induction heaters generally. These differences are attributable to: the nature of the heated substance (liquid, gas, or a mixture thereof), dynamic properties of the substance (stationary or moving liquid or gas), contacting surface shape and area, and the shape and location of any insulation. When heating liquids and gases, it is most advantageous to utilize a heating element that addresses some aspects of fluid dynamics (e.g. laminar flow, turbulent flow, fluid adhesiveness, cohesiveness, viscosity (and inviscid flow), friction and pressure loss, steady and unsteady flow, fluid velocity, and other fluid attributes) and the physical properties of the substances to be heated (melting point, boiling point, enthalpy, inductivity, properties of thermal expansion, and other physical properties). Heat transmission to liquids and gases is determined by the flow of fluid, fluid surface area, stirring phenomena (involving mixing of heated with relatively cooler liquid or gas), current speed of fluid, current volume, and mixing phenomenon. Further, as a liquid approaches its boiling point, the temperature difference between liquid and gas must be greater than 10° C. owing to gas generating phenomena, as gas produced at the heating surface forms a parting line which interferes with heating liquid not presently in contact with the heating element. Therefore, at a relatively proximal portion of the boiling point, it is especially necessary to foster stirring and mixture for the purpose of preventing degradation of heating efficiency.

Induction heaters require a relatively large heating area and use a plurality of coils and several converters to improve heating efficiency, as the heating area has limitations in relation to reactance value. Other problems exist with typical nichrome wire resistance-based heating elements including limitations on durability, the need for maintenance, the need to provide a protective covering, and nichrome wire degradation. Additionally, utilization of high output power results in increasing probability of a broken wire when using a plural heater. Moreover, to prevent unhelpful radiation of heat, it is necessary to consider insulation, which increases manufacturing costs, contributes to structural complexity, adds to running costs, and decreases heating efficiency. Furthermore, when heating liquids and gases, limitations in the available heat transfer area result in a decrease in heating efficiency. No known prior art transformer-based heating apparatus improves heating efficiency using heating methods disclosed herein.

SUMMARY

The present invention relates to an apparatus for heating liquids and gases generally, and more specifically to an apparatus utilizing one or more strategies, alone or in varied combinations, to improve heating efficiency. Example strategies include: use of a preferred heating element to enhance contact between the heating element and the subject liquid or gas, utilization of a smaller heating element (reduction of thermal radiation area), utilization of one or more disc filters disposed within the heating element, use of an inverter permitting location of the heating element outside the transformer, utilization of conductive wire extended from secondary winding of a transformer to serve as heating element, and cancellation of reactive currents by interfering reactive currents where appropriate, (prevention of electric loss by utilization of reactive currents). One aspect of the invention permits a greater efficiency in electric heat generation. Another aspect of the invention permits the heating apparatus to be produced in a variety of sizes and adapted for variety of applications requiring efficient heating of liquids or gases. In addition, another aspect of this invention provides for a heating element that is less subject to heating element breakage or degradation.

BRIEF DESCRIPTION OF THE DRAWINGS

FIG. 1 is a schematic of an embodiment apparatus utilizing the secondary winding as the heating element.

FIG. 2 is a schematic of an embodiment apparatus.

FIG. 3 is a schematic of an embodiment apparatus utilizing a substantially straight heating element.

FIG. 4 is a schematic of an embodiment apparatus utilizing a heating element substantially coiled back around a relatively proximal portion of inflow piping.

FIG. 5 is a schematic of an embodiment apparatus utilizing a reverse coil to cancel inductive interference.

FIG. 6 is a schematic of an embodiment apparatus utilizing a reverse coil connected with the fluid ingress point on the same polar side with an electric wire coupled to the end of the secondary coil.

FIG. 7 is a schematic of an embodiment apparatus utilizing a heating element shaped to define a container.

FIG. 8 is a schematic of an embodiment apparatus utilizing a heating element comprised of doubly folded pipe.

FIG. 9 is a schematic of an embodiment apparatus utilizing a heating element illustrating a primary coil disposed within a heating element.

FIG. 10 is a partial cross-section taken through line 10-10 of FIG. 9.

FIG. 11 is an embodiment annular disc filter utilized within the apparatus shown in FIG. 9. and certain other embodiments.

FIG. 12 is a cross-section taken through line 12-12 of FIG. 11.

FIG. 13 is a front view illustrating an embodiment disc filter.

FIG. 14 is a cross-section taken through line 14-14 of FIG. 13.

FIG. 15 is a front view illustrating an embodiment disc filter.

FIG. 16 is a cross-section taken through line 16-16 of FIG. 15.

FIG. 17 is a cross-section of an example embodiment heating element illustrating example embodiment inner surface.

FIG. 18 is a table demonstrating select example embodiment heating apparatus test results.

FIG. 19 is an embodiment straight formed heating element.

FIG. 20 is an embodiment spiral formed heating element illustrating an embodiment spiral rod, spiral pipe, or spiral planar surface.

FIG. 21 is a top view of an embodiment parallel heating element.

FIG. 22 is a side view of an embodiment parallel heating element.

FIG. 23 is a top view of an embodiment U-shaped heating element.

FIG. 24 is a side view of an embodiment U-shaped heating element.

FIG. 25 is a top view of an embodiment flat heating element.

FIG. 26 is a side view of an embodiment flat heating element.

FIG. 27 is a top view of an embodiment heating element.

FIG. 28 is a side view of an embodiment heating element.

FIG. 29 is a cross-sectional view taken through line 29-29 of FIG. 28.

FIG. 30 is a top view of an embodiment U-shaped heating element.

FIG. 31 is a side view of an embodiment U-shaped heating element.

DETAILED DESCRIPTION OF EMBODIMENTS OF THE INVENTION

Referring now to a first example embodiment apparatus illustrated by FIG. 1, the apparatus generally 5 is comprised of a transformer 10 having a primary winding 15, wound about a ferromagnetic core (not shown). Winding 15 is coupled to power source 20, and optionally coupled to inverter 25. When current flows through primary winding 15, magnetic flux is induced in secondary winding 30 (which, in this embodiment, also serves as heating element 32a) whereby current may flow in a completed circuit. Fluid (liquid or gas) enters the apparatus through fluid ingress point 35 and travels through inflow extension piping 40a. Inflow extension piping 40a transitions into a coiled conduit forming secondary winding 30/heating element 32a, and thereafter resumes a substantially straight course, transitioning into outflow extension piping 45a. Outflow extension piping 45a continues to fluid egress point 50. The alienation side of transformer 10 is shorted by placing electrical contact 52 between extension piping 40a and piping 45a, permitting current to flow through the alienation side of transformer 10. As current passes through the alienation side of transformer 10, secondary winding 30 is heated, transmits heat to fluid contained therein, and thereby functions as a heating element. Secondary winding 30/heating element 32a has an adequate resistance to permit heat to be generated therein, and in one preferred embodiment the resistance is in the range of 1.6730μΩ-cm to 185μΩ-cm. Generally, Ohm's law limits the maximum value of current which can flow through a heating element; current in excess of that maximum may cause the heating element to be rapidly heated and melted.

Regarding the flow of fluid, fluid enters ingress point 35, travels through piping 40a, enters secondary winding 30/heating element 32a, wherein fluid is heated as it moves through secondary winding 30/heating element 32a. Fluid exits secondary winding 30/heating element 32a and enters piping 45a, and exits the apparatus through egress point 50.

When the apparatus is used as a residential water heater, ingress point may be coupled to a pressurized city water line which would provide adequate flow through the system. Where the apparatus is used in other settings, flow may be provided through a variety of means including positive pressure providing inflow, negative pressure providing outflow, gravity feed, or any other means allowing liquid or gas to move through heating element 32.

In addition, this invention discloses a means for promoting heat transfer to liquid and gas within a heating element. As an example, illustrated by FIGS. 11-16, one or more disc filters 55 may be disposed inside the inner aspect of various embodiments of heating element 32. Disc filter 55 is, in one embodiment, substantially round and includes a plurality of filtering crosspieces G oriented uniformly across the plane of the filter. Disc filter 55 has a locking means to maintain the filter in a specific orientation when used with one or more disc filters. Specifically, in one embodiment, the locking means is comprised of a disc filer 55 shaped to define projections 65 disposed substantially circumferentially on one surface and corresponding recesses 60 on the other surface. The projection 65 of a first disc filter may be securely fitted into recess 60 of a second disc filter. The orientation of crosspiece G may be selected in a range of 0-90 (or is it 0-315, 0-337.5) degrees to vary the filtering capability of the disc filter combination. Several additional disc filters may be affixed together to promote multidirectional flow further aiding fluid mixing and enhancing the transfer of thermal energy from relatively warmer to relatively cooler fluid.

To change crossing angle 75 between crosspiece G of a first disc filter 55 and crosspiece G of a second disc filter 55, projection 65 of first disc filter 55 is disengaged from recess 60 of second disc filter 55, and the crossing angle 75 between the two filters aligned to: 0°, 45°, or 90°, (for filters 55a and 55c) or 0°, 22.5°, 45°, 67.5°, and 90° (for filter 55b). Projection 65 then inserts into recess 60 corresponding to the new crossing angle 75, maintaining disc filters 55 in place. It should be noted that the disclosed locking means is for illustrative purposes only, and a number of methods are known in the prior art, where filter repositioning is desirable, to provide permanent or semipermanent affixation between discs repositionable in the range of 0-359° wherein the repositioning may be manual or automated. Also, while a two disc filter combination has been illustratively described, a plurality of disc filters can be used successively, one after another, each changing the angle of crosspiece G relative to the first disc 55. This successive stacking of disc filters 55 permits fluid to be directed and redirected continuously and precisely throughout heating element 32. Where a plurality of disc filters 55 are equipped in heating element 32, changing the crossing angle of crosspiece G, one after another, stirring and mixing of stagnation, has a favorable impact on fluid (liquid and gas) heating.

The selection of disc filters 55 is made with consideration given to the fluid dynamics of the substance to be heated and physical attributes of the fluid, and the size, position, location, filtering orientation, and other parameters of disc filters 55. In a preferred embodiment, one or more disc filters 55 (a, b, and c) can be freely adjusted to optimize fluid heating and customized for utilization with one or more specific subject fluids. In an alternative embodiment, the number, position, and orientation of one or more disc filters 55 (a, b and c) is pre-selected during the manufacturing process to provide optimum heating of specific liquid and gas to be heated. In a further embodiment, one or more disc filters 55 may be used outside heating element 32 but along the fluid flow path (e.g. inflow piping 40a outflow piping 45a as illustrated by FIG. 1)

to continue mixing, stirring and thermal energy transfer after the fluid has left heating element 55.

For an example use within heating element 32, disc filters 55 illustrated by FIGS. 13, 14 and FIGS. 15, 16 may be equipped within heating element 32 (*a, b, c, d*, or *e*). Disc filter 55 (a, b, or c) preferably has a resistance in the range of 1.6730 μΩ·cm to 185 μΩ·cm, and further aids in stirring the liquid and gas to expand the heated area. Generally, one or more disc filter 55 (*a, b*, or *c*) may be inserted into one or more points to serve as the first disc to set subsequent disc filters (a, b, or c) fixedly thereupon; ringed stoppers may be disposed within said heating element 32 and positioned on either side of one or more disc filters 55, maintaining them in place.

As each heating element has a different diameter and length, corresponding, in part, to fluid volume and output power, the size, number, shape, and composition of disc filters 55 will vary and may advantageously tailored to a particular heating element and subject fluid.

As a means to stir fluid liquid and promote the heat transfer, a plurality of disc filters can be optionally used in combination with any heating element hereindisclosed, and heating element 32(*a, b, c, d* and *e*) or 32*g* may be filled with several disc filters, including tens of filters.

Moreover, as an aspect of this invention, corresponds to the nature of liquid and gas fluid (viscosity, melting point, boiling point, enthalpy, rate of heat transmitting and coefficient of expansion), the shape, thickness, width and pitch, of crosspiece G, as illustrated by FIGS. 11-16, is specifically helpful in directing fluid path through heating element 55 and may be tailored to varied specific fluids and desired heating applications. Additionally, the length of projection 65 may be increased to change the space between one or more successive disc filters 55, and can further refine control over fluid path within heating element 32. Additionally, an exemplar crosspiece G is depicted by FIGS. 12, 14, and 16 is triangular/pyramidal in shape, however, it should be noted that crosspiece G may be round, angled, corrugated, oval, lozenge-shaped, or further tailored to impact fluid behavior as it moves through heating element 32.

In an example embodiment, as illustrated by FIGS. 11-16 one or more disc filters 55 may be disposed within secondary winding 30/heating element 32*a*. Disc filters 55 preferably have a resistance in the range of 1.6730 μΩ·cm to 185 μΩcm and aid in expanding the heating surface area. One or more disc filters 55 are inserted within several points of heating element pipe 32*a*, and ringed stoppers (not shown) may be utilized on either side of disc filter 55, to maintain one or more filters 55 in place. Disc filter 55 is typically set perpendicular to the long-axis of the heating element 32, however setting angle may vary. Disc filter 55 size, position, number, location, filtering orientation, setting angle may be tailored to various substances to be heated, heating element 32 shape, sizes, and configurations, fluid flow characteristics, and heating apparatus settings.

In another embodiment, the filtering orientation, location and number of disc filters 55 are fixed and preselected during the manufacturing process considering the particular liquid or gas to be heated. The use of disc filters 55 as a means of stirring fluid may be optionally used with each of the embodiments described in the present invention. Any number of disc filters 55 may be utilized and in one example the heating element 32*a* may be filled with dozens of such filters. Importantly, while a particular disc filter 55 structure has been identified, the present invention is not limited to the use of one particular type of filter.

Moreover, this invention uses the resistance of heating element's cross-sectional area preferably in the range of 1.6730 μΩ·cm to 185μΩcm, using a transformer corresponding to large or small output power, with keeping safety as a heating apparatus to correspond to the large or small output power. Thus, this invention can flow large electric current at low Voltage, and form several tens Watt (W) to several hundreds KW heating apparatus can be made as illustrated by FIGS. 1, 2, 3, 4, 5, 6 and 7. Also, without regulation in Voltage, heating element with several thousand KW can be made as illustrated by FIGS. 2, 3, 4, 5 and 6.

Moreover, this invention discloses various embodiment heating elements 32 illustrated by FIGS. 1, 2, 3, 4, 5, 6, 7 and 8 and various type of deformed heating elements 32.

Further, the present invention discloses an additional means for promoting turbulent flow where the heating element's 32 inner aspect is nonsmooth and may be shaped to foster liquid/gas shear and stirring thus promoting turbulent flow (stirring, and mixture) thereby aiding in heat transfer. In one example, FIG. 17 illustrates a means to promote turbulent flow (stirring and mixture) within heating element 32. To promote turbulence, convexities or notches 77 exist in the inner surface of heating element 32. Concavities or depressions 39 which may be used s well. FIG. 17 illustrates the two used together, however, it should be noted that heating element 32 may be used with either notches 77 or depressions 39. Importantly, FIG. 17 illustrates one embodiment: any non-smooth surface or shape of the innermost aspect of the heating element that promotes turbulent flow (stirring and mixture) may be utilized and only a portion of the innermost surface may be used to disrupt laminar flow.

In a non-limiting series of example experiments, heat efficiency of a geyser output from an example coffee machine was examined. The Voltage used was 110-140, the output power was 1.1-1.4 Kw. Secondary winding 30 served as heating element 32*a* and was comprised of stainless steel. (550 W~700zW X2 series). The inside diameter of secondary winding 30/heating element 32*a* is 10 mm, and the outside diameter is 12 mm; the length of pipe is 4.5 m aggregate. A series (Voltage about 6V~ Currents: about 83 A~) X2 was used. The measurement tools were: a digital fluid volume meter, 2 digital thermometers (for measuring water supply temperature and thermal output). An ammeter, voltmeter, voltage adjustment meter, and solenoid-controlled valve were also utilized. This experiment did not use disc filters 55 or inverter 25. The output volume was 80 cc, the output interval time: 1-2 seconds. Results: The time from start to output of hot water was 1 minute 54 seconds. Given input power 1,100 wh 80 cc for 20 sec, the change starting water temperature from 15° C. resulted in water at 73.9° C. without insulation and 75.4° C. with forming resin insulation placed on the heating element. The relationship of power and time to get 80 cc of water starting at 15° C. to 80° C. was between 21.1-21.9 seconds where 1,100 W was used; 19.5 seconds where 1,200 W of power was used; 17.4-18.2 seconds where 1,300 W of power was used; and 16.2-16.5 seconds where 1,400 W of power was used, as reflected in Table 1. below.

TABLE 1

| | Input of Electric Power W | | | |
|---|---|---|---|---|
| | 1,100 | 1,200 | 1,300 | 1,400 |
| Time (seconds) | 21.1-21.8 | 19.5 | 17.4-18.2 | 16.2-16.5 |

FIG. 18 shows examples of the heating apparatus effectiveness for differing power in KW, differing water starting temperatures, and differing volume of water heated in one minute. The results illustrate the output volume and temperature, thermal efficiency being 95-99%. The experiment examined the use of four different power settings: 10 KW, 12 KW, 15 KW, and 20 KW. The experiment utilized water at four supply temperatures: 5° C., 10° C., 15° C., and 20° C. Different volumes of water were passed through the heating apparatus per minute: 3 liters, 4 liters, 5 liters, 6 liters, 7 liters, and 8 liters. Thus, FIG. 18 illustrates results considering three variables: power, starting water temperature, and quantity of water/minute; heated water temperature was recorded for each combination By way of clarification, in the first embodiment described above, secondary winding 30 functions as the heating element 32a. In the remainder of the example embodiments to follow, heating element 32 is distinct from secondary winding 30.

Referring now to a second example embodiment apparatus illustrated by FIG. 2, the apparatus, generally 5, is comprised of a transformer 10 having a primary winding 15 coupled to power source 20. Power source 20 is optionally coupled to inverter 25. When current flows through primary winding 15, magnetic flux is induced in secondary winding 30. Fluid or gas enters the apparatus through fluid ingress point 35 and travels through heating element 32b and exits through egress point 50. Heating element 32b is placed in electrical contact with secondary winding 30 through wire 42 at one end and wire 47 at the other end. As current passes through the alienation side of the transformer, heating element 32b has an adequate resistance to permit heat to be generated therein.

In a third example embodiment, as illustrated by FIG. 3 and FIG. 19, heating element 32c is comprised of substantially straight pipe or rods, as illustrated in FIG. 19, and has an adequate resistance to permit heat to be generated therein. As more fully described above, disc filters 55 may be disposed within heating element 32c to promote turbulent flow and enhance fluid heating. In addition, as more fully described above, the inner aspect of the heating element 32 may be non-smooth to promote turbulent flow and enhance fluid/gas heating.

In a fourth example embodiment, as illustrated by FIG. 4, inflow piping 71 coupled to ingress point 35. Inflow piping 71 transitions to form spiral heating element 32d. Next, said spiral heating element 32d is substantially coiled back around a relatively proximal portion of inflow piping 71. Coiled heating element 32d transitions into outflow piping 85 which carries heated fluid to egress point 50. This embodiment offers the advantage of permitting magnetic flux generated in coiled heating element 32d to heat a portion of inflow piping 71, and thus enhance heating efficiency utilizing magnetic flux caused to void power (loss of power).

In the fifth embodiment, as illustrated by FIG. 5, a reverse coil 80a is utilized to cancel inductive interference from the secondary winding 30. In this embodiment, electromagnetic inductance, generated in the conductor heating element 32e, can be cancelled by the electromagnetic inductance generated from reversible coil 80a: the closed circuit of the secondary side being comprised of secondary coil 30, extending part 95, electric wire 42, heat element 32e, electric wire 47, reversible coil 80a, and electric wire 100. The heating element 32e, then may be heated by resistance-based heating exclusively and has the advantage of avoiding the generation of interfering reactant current. In an alternative embodiment, illustrated by FIG. 6, reverse coil 80b is connected with the fluid and/or gas ingress point 35 on the same polar side with electric wire 42, connected with the end of the secondary coil 30.

In a sixth example embodiment, as illustrated by FIG. 7, the heating element 32f, is shaped to define a container, the upper end being open, through which current may pass.

In a seventh example embodiment, as illustrated by FIG. 8, power source 20 is coupled, optionally to inverter 25, which is coupled to primary winding 15. Transformer 10 is equipped to make voltage pressurization or decompression. When current flows through winding 15, magnetic flux is induced and heat is produced in heating element 32g. Fluid (liquid or gas) is introduced through ingress point 35 and travels through inflow piping 40b, is heated in heating element 32g, passes through outflow piping 45b, and exits through egress point 50. As more fully described above, one or more disc filters 55a may be disposed within heating element 32g to promote turbulent flow and enhance fluid/gas heating. In addition, as more fully described above, the inner aspect of the heating element 32g may be non-smooth to promote turbulent flow and enhance fluid/gas heating.

In an eighth example embodiment, illustrated by FIG. 9, primary winding 15 is wound around core of transformer 12. An annular disc filter 55a is disposed within inner heating element 32h. FIG. 10 illustrates disc filters 55a occupying the inner space of heating element 32h. The heating apparatus 5 preferably has a single-phase conductor. Heating element 32h is comprised of doubly folded pipe divided at two points and connected by contacting pipe 90. Fluid enters apparatus 5 at ingress point 35, through inflow piping 40c, travels through the first portion of heating element 32h, flow is redirected through disc filters 55a, thereafter exits heating element 32h, and moves through contacting pipe 90, into the second portion of heating element 32h, through outflow piping 45c, and out egress point 50. When current passes through primary winding 15, eddy current is generated in heating element 32h, heating the same through electromagnetic inductance. As more fully described above, disc filters 55a may be disposed within heating element 32h to promote turbulent flow and enhance fluid/gas heating. In addition, as more fully described above, the inner aspect of the heating element 32h may be non-smooth to promote turbulent flow and enhance fluid/gas heating.

Regarding resistance, in the above disclosed embodiments, a useful resistance range for heating element 32 has been found to be in the range of 1.6730 μΩ-cm to 185 μΩ-cm. Heating elements utilized in present invention, however, are not limited exclusively to this range. The resistance of the heating element is directly related to the length of the heating element and inversely related to the cross-sectional area. Heating element 32 can be freely designed for utilization within a large or small heating apparatus befitting a particular applied need for heated liquids or gases.

Regarding the example embodiments discussed above, one or more means for mixing or stirring fluid or gas may be utilized. For example as more fully described above, one ore more disc filters 55 may be disposed within heating element 32 embodiments listed above to promote turbulent flow and enhance fluid/gas heating. In addition, as more fully described above, the inner aspect of the heating element 32 embodiments described above may be non-smooth to promote turbulent flow (stirring and mixture) and enhance fluid/gas heating. These exemplar thermal transfer facilitating means may be utilized individually or together; these exemplar heating means may also be utilized with other means to promote fluid stirring and mixing.

It should be noted that the term, fluid as used herein denotes liquid, gas, or a combination thereof. Additionally, any substance containing particles, or a semisolid that will move apparatus 5 and heating element 32 may be heated with the present invention.

Regarding power source 20, in one embodiment, power source 20 is a single phase power source. In an alternative embodiment, power source 20 is a three-phase power source. Power source, 20 may be alternating current or direct current and may be electrically coupled to an inverter 25. In one embodiment, inverter 25 is omitted. To enhance safety, it is helpful to maintain current under 24 volts. Transformer 10 may be equipped to make voltage pressurization or decompression. Various voltage supplied to a transformer is from 100 volts to several ten thousand volts. Supplied power is from several kilowatt to several ten thousand kilowatt.

Regarding materials utilized for the heating element, copper, aluminum, stainless steel, stainless alloyed steel, titanium, titanium alloyed, nickel, nickel alloyed, silver, and other conductive metals capable of serving as a metallic conduit which may function as a resistance based heating element, in a preferred embodiment having a resistance in the range of 1.6730 $\mu\Omega$-cm to 185 $\mu\Omega$-cm.

Regarding the size and shape of heating element 32, many different options may be utilized to permit the apparatus to be utilized for a range of applications. Heating element 32c in one embodiment illustrated by FIG. 19 is a substantially straight pipe or solid rod. In another embodiment illustrated by FIG. 20, heating element 32 may be comprised of a spiral rod 32i, spiral pipe 32j, or spiral planar element 32k which offers the advantage of an increased area for thermal exchange. In another example embodiment, illustrated by FIGS. 21 and 22, the heating element 32l is comprised of a plurality of parallel conductive rods, pipes, or planar surfaces which function as heating element members and offer the advantage of enhanced surface area for thermal exchange. In FIGS. 21-23, X represents the width of the heating element member, Z represents the distance between heating element members, and Y represents the height of the heating element member, where with a flat element: X>Y or X<Y. For squared heating element members: X=Y. In yet another example embodiment, as illustrated by FIGS. 23 and 24, heating element 32m is comprised of a U-shaped (or serpentine) conductor which offers the advantage of countercurrent thermal exchange. In other embodiments, as illustrated by FIGS. 25 and 26, heating element 32n is comprised of a flat planar plate (e.g. iron plate or grill) over which fluid passes. Planar plate heating element 32n is particularly useful for heating large containers of pharmaceuticals, can be adapted to use in an apparatus to provide hot water for noodles, may be utilized as a warm air circulator, and may be used for indirect heating of a semi-conductor. In another example embodiment, as illustrated by FIGS. 27-29, heating element 32o is comprised of a partial rectangle providing heating on three sides and increased heating surface area. In another embodiment illustrated by FIGS. 30-31, heating element 32p utilizes copper contact connection point 99 providing the benefit of easy coupling points for fluid supply and exhaust. Secondly, where copper wire and stainless steel is connected around the outer aspect of piping, connection resistance generates at the copper connection point 99 and connection point 99 is more robustly heated relative to the remainder of the heating element. Advantageously, more uniform heating of the heating element, and improved apparatus efficiency, is achieved by increasing of connection point 99 surface area, as expansion of connection area decreases connection resistance. Thirdly, disc filter 55 may be utilized along inner diameter of the connection point.

In yet another embodiment, heating element 32 is a series of rectangular metallic sheets. In another embodiment, heating element 32 is a pyramidal shape. In yet another embodiment, heating element 32 may be comprised of a plurality of wire rods.—which may be useful for, among other things, resin mold heating. One or more disc filters 55 may be utilized within the space of any heating element 32 having a void to accommodate the same. Moreover, while the embodiment disc filters 55 have been disclosed, the invention specifically is not limited to filters in any particular shape.

Additionally, the heating element may be coated with inorganic matter (e.g. ceramic or glass), an organic coating (e.g. silicon and Teflon) and inorganic matter used with mixture. This coating may be combination with organic and inorganic matter disposed inner surface of heating element 32: as in the Sol Gel method. Additionally, the heating element may be insulated with resin insulation (spray) and inorganic insulation (paint) offering increased thermal efficiency in circumstances where desired and appropriate.

Regarding a few example applications for the present invention, heating apparatus 5 can be used as a water heater, a floor heater, a home air heater, a saturated steam generating device, a drier, a coffee or tea maker, a vending machine, a hot water supply, cooking applications, (heat boil) and steam beauty apparatus, medical apparatus, and other heating applications.

Although the present invention has been described with reference to the preferred embodiments, it should be understood that various modifications and variations can be easily made by those skilled in the art without departing from the scope and spirit of the invention. Accordingly, the foregoing disclosure should be interpreted as illustrative only and is not to be interpreted in a limiting sense. It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

What is claimed is:

1. A heating apparatus comprising:
    a transformer, said transformer having a core, a primary winding associated with said core and adapted to generate an alternating magnetic field in the presence of an alternating power current passing through said primary winding and a secondary winding; wherein both ends of secondary winding are shorted to form a closed circuit and wherein at least a portion of said secondary winding forms a conductive heating element having a resistance in the range of 1.6730 $\mu\Omega$cm to 185 $\mu\Omega$cm, wherein said heating element is hollow permitting fluid to pass therethrough;
    one or more disc filters disposed within said heating element, wherein said filtration promotes turbulent fluid flow and fluid mixture within said heating element.

2. The heating apparatus according to claim 1, further comprising one or more inverters electrically coupled to said power source and electrically coupled to said primary coil.

3. The heating apparatus according to claim 1, wherein the inner surface of said heating element is nonsmooth, wherein turbulent flow is promoted.

4. A heating apparatus comprising:
    a transformer, said transformer having a core, a primary winding associated with said core and adapted to generate an alternating magnetic field in the presence of an alternating power current passing through said primary winding and a secondary winding;

a heating element electrically coupled to said secondary winding wherein said heating element forms a completed circuit, said heating element having a resistance in the range of 1.6730 μΩcm to 185 μΩcm, wherein said heating element is hollow permitting fluid to enter and exit said heating element through an ingress point and egress point respectively;

one or more disc filters disposed within said heating element, wherein said filters promote turbulent flow and mixing of fluid within said heating element.

5. The heating apparatus according to claim 4, further comprising one or more inverters electrically coupled to said power source and electrically coupled to said primary coil.

6. The heating apparatus according to claim 4, wherein the inner surface of said heating element is nonsmooth, wherein turbulent flow is promoted.

7. The heating apparatus according to claim 4, wherein said heating element is substantially straight.

8. The heating apparatus according to claim 4, wherein said heating element is substantially coiled.

9. The heating apparatus according to claim 4, wherein said heating element is comprises a plurality of parallel rectangular elements.

10. The heating apparatus according to claim 4, wherein said heating element follows a substantially serpentine path.

11. The heating apparatus according to claim 4, wherein the inner aspect of said heating element is coated with inorganic matter.

12. The heating apparatus according to claim 11, wherein said inorganic matter is: ceramic or glass.

13. The heating apparatus according to claim 4, wherein the inner aspect of said heating element is coated with an organic matter.

14. The heating apparatus according to claim 13, wherein said organic matter is a macromolecule.

15. The heating apparatus according to claim 4, further comprising ingress tubing coupled to ingress point and egress tubing coupled to egress point, wherein said heating element is substantially coiled back around a relatively proximal portion of ingress tubing, wherein said coiled heating element generates reactive current, said reactive current further heating fluid contained within said relatively proximal portion.

16. A heating apparatus comprising:

a transformer, said transformer having a core and a power supply, a primary winding wound around said core of said transformer;

a heating element disposed outside the circumference of said primary winding, said heating element comprised of a first portion and second portion, the first portion and second portion being coupled to permit fluid to flow therebetween;

at least one disc filter, defined as having an annular void, disposed around said core wherein said core passes through said annular void, wherein said filter is disposed within said heating element, occupying the space between said primary winding and said heating element;

a fluid ingress point coupled to said first portion of heating element;

a fluid egress point coupled to said second portion of said heating element;

wherein current passing through primary winding induces eddy current generated in heating element, heating the same through electromagnetic inductance, wherein fluid entering through ingress point, passing through heating element, and exiting through egress point is heated.

* * * * *